United States Patent
Dai et al.

(10) Patent No.: US 11,034,728 B2
(45) Date of Patent: Jun. 15, 2021

(54) PEPTIDES FOR BINDING EPIDERMAL GROWTH FACTOR

(71) Applicant: 3M INNOVATIVE PROPERTIES COMPANY, St. Paul, MN (US)

(72) Inventors: Minghua Dai, Plymouth, MN (US); Amy K. McNulty, Stillwater, MN (US); Federica Sgolastra, St. Paul, MN (US); Jie Liu, Woodbury, MN (US); Jana Ninkovic, St. Paul, MN (US); Robert T. Fitzsimons, Jr., Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 26 days.

(21) Appl. No.: 16/339,085

(22) PCT Filed: Sep. 28, 2017

(86) PCT No.: PCT/US2017/053958
§ 371 (c)(1),
(2) Date: Apr. 3, 2019

(87) PCT Pub. No.: WO2018/067371
PCT Pub. Date: Apr. 12, 2018

(65) Prior Publication Data
US 2020/0181198 A1 Jun. 11, 2020

Related U.S. Application Data

(60) Provisional application No. 62/404,510, filed on Oct. 5, 2016.

(51) Int. Cl.
*C07K 7/08* (2006.01)
(52) U.S. Cl.
CPC ................................. *C07K 7/08* (2013.01)
(58) Field of Classification Search
None
See application file for complete search history.

(56) References Cited

U.S. PATENT DOCUMENTS

| | | | |
|---|---|---|---|
| 5,218,090 A | 6/1993 | Connors |
| 6,887,844 B1 | 5/2005 | Ronn |
| 7,534,240 B1 | 5/2009 | Johnson |
| 8,529,897 B2 | 9/2013 | Washburn |
| 8,624,077 B2 | 1/2014 | Rosenberg |
| 2009/0081797 A1 | 3/2009 | Fadeev |
| 2012/0276039 A1 | 11/2012 | Courage |

OTHER PUBLICATIONS

Altschul, "Basic local alignment search tool", J. Mol. Biol, 1990, vol. 215, No. 3, pp. 403-410.
Altschul, "Gapped BLAST and PSI-BLAST: a new generation of protein database search programs", Nucleic Acids Res, 1997, vol. 25, No. 17, pp. 3389-3402.
Ausubel, "Current Protocols in Molecular Biology", Greene Publishing Associates and John Wiley & Sons, 1994, Table of contents, 25pages.
Drescher, "Surface plasmon resonance (SPR) analysis of binding interactions of proteins in inner-ear sensory epithelia", Methods Mol Biol., 2009; vol. 493, pp. 323-343.
Gowda, "Topical application of recombinant platelet-derived growth factor increases the rate of healing and the level of proteins that regulate this response", Int Wound J 2015, vol. 12, No. 5, pp. 564-571.
Guardiola, "Peptides targeting EGF block the EGF-EGFR interaction", ChemBioChem, 2016, vol. 17, No. 8, pp. 702-711.
Higgins, "Clustal W: improving the sensitivity of progressive multiple sequence alignment through sequence weighting, position-specific gap penalties and weight matrix choice", Nucleic Acids Res, 1994, vol. 22, No. 22, pp. 4673-4680.
Karlin, "Applications and statistics for multiple high-scoring segments in molecular sequences", Proc. Natl. Acad. Sci., 1993, vol. 90, No. 12, pp. 5873-5877.
Karlin, "Methods for assessing the statistical significance of molecular sequence features by using general scoring schemes", Proc. Natl. Acad. Sci. USA, 1990, vol. 87, No. 6, pp. 2264-2268.
Patching, "Surface plasmon resonance spectroscopy for characterization of menrane protein-ligand interactions and its potential for drug discovery", Biochim Biophysica Acta, 2014, vol. 1838, pp. 43-55.
Sambrook, "Molecular Cloning, a Laboratory Manual", 2d edition, Cold Spring Harbor Press, 1989, Table of contents, 34 pages.
Shagaghi, "Archtypal tryptophan-rich antimicrobial peptides: properties and applications" Worlds J Microbiol Biotechnol, 2016, vol. 32, No. 2, 10pages.
Stanirowski, "Growth factors, silver dressings and negative pressure wound therapy in the management of hard-to-heal postoperative wounds in obstetrics and gynecology: a review", Arch Gynecol Obstet, 2015, vol. 292, No. 4, pp. 757-775.
International Search report for PCT International Application No. PCT/US2017/053958 dated Jan. 29, 2018, 6 pages.

*Primary Examiner* — Sergio Coffa
(74) *Attorney, Agent, or Firm* — Qiang Han

(57) ABSTRACT

A polypeptide having a sequence at least 70% identical to SEQ ID NO: 1 (YVSPGMKNVNWWSHWWHATD) is provided. The polypeptide includes no more than 100 total amino acid residues.

13 Claims, No Drawings
Specification includes a Sequence Listing.

PEPTIDES FOR BINDING EPIDERMAL GROWTH FACTOR

FIELD

Peptides for binding epidermal growth factor (EGF) are provided.

This application contains a sequence listing with the file name SequenceListing_ST25, created Oct. 5, 2016. The sequence listing file contains 729 bytes and is incorporated herein by reference in its entirety.

BACKGROUND

Clinical studies and practice have shown that providing a negative pressure in proximity to a tissue site promotes the growth of new tissues at the tissue site. The application of negative pressure is successful in treating wounds. This treatment (frequently referred to in the medical community as "negative pressure wound therapy (NPWT)," "reduced pressure therapy," or "vacuum therapy") provides a number of benefits, including faster healing and increased formulation of granulation tissue. Typically, reduced pressure is applied to tissues through a foam, a pad or other manifolding device, such as gauze. The manifolding device typically contains cells, pores or other openings that are capable of distributing reduced pressure to the tissue and channeling fluids that are drawn from the tissue. The porous pad often is incorporated into a dressing having other components that facilitate treatment. EGF is one of the most important growth factors in wound healing. EGF promotes the proliferation and differentiation of fibroblast and epithelial cells.

SUMMARY

Conventional NPWT approach does not distinguish between beneficial factors (e.g. growth factors) and detrimental factors (e.g. inflammatory cytokines) while removing the wound exudate. The polypeptides of the present disclosure have high affinity to bind EGF and can retain EGF and sustain its release to maintain its activity, for example to promote the proliferation and differentiation of fibroblast and epithelial cells.

A polypeptide having a sequence at least 70% identical to SEQ ID NO: 1 (YVSPGMKNVNWWSHWWHATD) is provided. The polypeptide includes no more than 100 total amino acid residues.

Various aspects and advantages of exemplary embodiments of the present disclosure have been summarized. The above Summary is not intended to describe each illustrated embodiment or every implementation of the present disclosure. Further features and advantages are disclosed in the embodiments that follow. The Detailed Description that follow more particularly exemplify certain embodiments using the principles disclosed herein.

Definitions

For the following defined terms, these definitions shall be applied for the entire Specification, including the claims, unless a different definition is provided in the claims or elsewhere in the Specification based upon a specific reference to a modification of a term used in the following definitions:

The terms "DNA" and "DNA sequence" are interchangeable and not intended to be limiting. "DNA" shall have the meaning known in the art and include genomic DNA, cDNA, or plasmid DNA, It may be in a wide variety of forms, including, without limitation, double-stranded or single-stranded configurations, circular form, plasmids, relatively short oligonucleotides, peptide nucleic acids also called PNA's and the like. The DNA may be genomic DNA, which can include an entire chromosome or a portion of a chromosome. The DNA may include coding (e.g., for coding mRNA, tRNA, and/or rRNA) and/or noncoding sequences (e.g., centromeres, telomeres, intergenic regions, introns, transposons, and/or microsatellite sequences). The DNA may include any of the naturally occurring DNA as well as artificial or chemically modified DNA, mutated DNA, and the like.

The term "sample" refers to a starting material suspected of containing an allergen. Samples include, but are not limited to, food samples (including but not limited to samples from food intended for human or animal consumption such as processed foods, raw food material, produce (e.g., fruit and vegetables), legumes, meats (from livestock animals and/or game animals), fish, sea food, nuts, beverages, drinks, fermentation broths, and/or a selectively enriched food matrix comprising any of the above listed foods), water samples, environmental samples (e.g., soil samples, dirt samples, garbage samples, sewage samples, industrial effluent samples, air samples, or water samples from a variety of water bodies such as lakes, rivers, ponds etc.), air samples (from the environment or from a room or a building), clinical samples, veterinary samples, forensic samples, agricultural samples, pharmaceutical samples, biopharmaceutical samples, samples from food processing and manufacturing surfaces, and/or biological samples.

"Test Method A" refers to the following general surface plasmon resonance (SPR) binding assay. Target protein (e.g., EGF and TNF-□) is immobilized at 25° C. and diluted peptides are injected for 3 min at a flow rate of 10 μl/min at 25° C. Binding assay is performed according to detailed Test method A in Examples.

DETAILED DESCRIPTION

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

As used in this Specification, the recitation of numerical ranges by endpoints includes all numbers subsumed within that range (e.g. 1 to 5 includes 1, 1.5, 2, 2.75, 3, 3.8, 4, and 5, and the like).

The terms "polypeptide" and "peptide" are interchangeable and not intended to be limiting. The polypeptides of the present disclosure are useful for binding EGF. The binding affinity of the polypeptides to EGF can allow the polypeptides to absorb EGF from wound or serum fluid and concentrate EGF at the wound site to promote healing.

The present disclosure provides a polypeptide. In some embodiments, the peptide includes at least 5, at least 6, at least 7, at least 8, at least 9, at least 10, at least 11, at least 12, at least 13, at least 14, or at least 15 total amino acid residues. In some embodiments, the polypeptide includes no more than 100, no more than 50, no more than 40, no more than 30, no more than 20, no more than 19, no more than 18, no more than 17, no more than 16, or no more than 15 total amino acid residues. In some embodiments, the peptide sequences generally include 5-100 amino acid residues. In some embodiments, the peptide sequences generally include 5-50 amino acid residues. In some embodiments, the peptide sequences generally include 7-40 amino acid residues. In some embodiments, the peptide sequences generally include 10-30 amino acid residues. In some embodiments, the peptide sequences generally include 10-20 amino acid residues.

In some embodiments, the polypeptide is at least 70% identical to YVSPGMKNVNWWSHWWHATD (SEQ ID NO: 1). In some embodiments, the polypeptide is at least 75% identical to SEQ ID NO: 1. In some embodiments, the polypeptide is at least 80% identical to SEQ ID NO: 1. In some embodiments, the polypeptide is at least 85% identical to SEQ ID NO: 1. In some embodiments, the polypeptide is at least 90% identical to SEQ ID NO: 1. In some embodiments, the polypeptide is at least 95% identical to SEQ ID NO: 1. In some embodiments, the polypeptide is 100% identical to SEQ ID NO: 1. In some embodiments, the polypeptide is at least 80% identical to KNVNWWSHWWHATD (SEQ ID NO: 2). In some embodiments the polypeptide is at least 85% identical to SEQ ID NO: 2. In some embodiments, the polypeptide is at least 90% identical to SEQ ID NO: 2. In some embodiments the polypeptide is at least 95% identical to SEQ ID NO: 2. In some embodiments, the polypeptide is 100% identical to SEQ ID NO: 2.

"Percent (%) amino acid sequence identity" refers to the percentage of amino acid residues in a candidate sequence that are identical with the amino acid residues in the reference sequence (e.g., SEQ ID NOs: 1 and 2) after aligning the sequences and introducing gaps, if necessary, to achieve the maximum percent sequence identity, and not considering any conservative substitutions as part of the sequence identity. A % amino acid sequence identity value is determined by the number of matching identical residues divided by the total number of residues of the "longer" sequence in the aligned region. The "longer" sequence is the one having the most actual residues in the aligned region. For example, for a polypeptide 80% identical to YVSPGMKNVNWWSHWWHATD (SEQ ID NO: 1), 80% of amino acid residues in the polypeptide are identical with the amino acid residues in YVSPGMKNVNWWSHWWHATD (SEQ ID NO: 1), after aligning the sequences and introducing gaps. That is, in a peptide having 20 residue "longer" sequence in the aligned region, for 80% identity to SEQ ID NO: 1, at least 16 residues will be identical to the amino acid residues in SEQ ID NO: 1, or, for 90% identity to SEQ ID NO: 1, at least 18 residues will be identical to with the amino acid residues in SEQ ID NO: 1, with the remaining being those selected according to the design choices given herein (e.g., addition of prolines, replacement of cysteine(s); inclusion of positively charged amino acids such as K and R.). In some embodiments, the polypeptide 80% identical to SEQ ID NO: 1 can be made by adding additional amino acids to either or both termini of SEQ ID NO: 1. In addition, the sequences (which may range from 10 to 29 amino acids in length) could be lengthened according to the known sequence of granulysin; or could be lengthened by "dimerization," or oligomerization, that is, repeating all or a portion of a helical sequence contained in a sequence given herein. In some other embodiments, such polypeptide 80% identical to SEQ ID NO: 1 can be made by substitution, deletion or insertion in SEQ ID NO: 1. The substitution can be made by chemical synthesis, or using any other suitable methods, such as oligonucleotide-mediated (site-directed) mutagenesis, and PCR mutagenesis. Substitution of D for L amino acids is also contemplated herein, but would not change the sequence identity. Substitution of 13 for a amino acids is also contemplated herein, but would not change the sequence identity. The present peptides may contain modifications, such as fatty acid extensions or other organic molecules. None of these modifications affect the sequence identity as defined herein.

To determine the percent identity of two amino acid sequences or of two nucleic acids, the sequences are aligned for optimal comparison purposes. The percent identity between two sequences can be determined by any suitable means, for example, techniques similar to those described below. In calculating percent identity, typically exact matches are counted. A gap, i.e. a position in an alignment where a residue is present in one sequence but not in the other, would count as a single mismatch. The identity referred to herein can be local sequence identity. That is, for example, if the reference sequence is 30 amino acids long and the test sequence is 14 amino acids long, only the 14 amino acids are considered, and gaps are allowed, as stated.

The determination of percent identity between two sequences can be accomplished using a mathematical algorithm. A nonlimiting example of a mathematical algorithm utilized for the comparison of two sequences is the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the BLASTN and BLASTX programs of Altschul et al. (1990) J. Mol. Biol. 215:403. BLAST nucleotide searches can be performed with the BLASTN program, score=100, wordlength=12, to obtain nucleotide sequences homologous to like nucleic acid molecules of the invention. BLAST protein searches can be performed with the BLASTX program, score=50, wordlength=3, to obtain amino acid sequences homologous to protein molecules of the invention. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) Nucleic Acids Res. 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™ GENE- DOC™ (Karl Nicholas) allows assessment of amino acid (or DNA) similarity and identity between multiple proteins. In some embodiments, sequence identity can be determined by the CLUSTAL-W program in MacVector version 6.5, operated with default parameters, including an open gap penalty of 10.0, an extended gap penalty of 0.1, and a BLOSUM 30 similarity matrix.

The polypeptides of the present disclosure may be synthesized using any suitable methods or techniques, such as by Solid-Phase Peptide Synthesis (SPPS). The polypeptides may be synthesized as "dendrimers", i.e., multiple peptides attached to a core. A method for synthesis of peptide dendrimers is provided, e.g., in "NCAM binding compounds," U.S. Pat. No. 6,887,844 (Ronn et al.). Alternatively, polypeptides of the present disclosure can be expressed recombinantly by introducing a nucleic acid encoding the polypeptide into host cells, which are cultured to express the polypeptide. Such polypeptides a may be partially or completely isolated or purified from the cell culture through any suitable protein purification techniques, such as cell tissue, organ fractionation, or chromatographic or electrophoretic techniques.

The present disclosure also provides a nucleic acid comprising a nucleic acid sequence encoding the polypeptides. Methods of preparing DNA and/or RNA molecules are well known in the art. In one aspect, a DNA/RNA molecule encoding a polypeptide provided herein is generated using chemical synthesis techniques and/or using polymerase chain reaction (PCR). If desired, a polypeptide coding sequence is incorporated into an expression vector. One of ordinary skill in the art will appreciate that any of a number of expression vectors known in the art are suitable, such as, but not limited to, plasmids, plasmid-liposome complexes, and viral vectors. Any of these expression vectors are prepared using standard recombinant DNA techniques described in, e.g., Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994). Optionally, the nucleic acid can be operably linked to one or more regulatory sequences, such as a promoter, activator, enhancer, cap signal, polyadenylation signal, or other signal involved with the control of transcription or translation. The present disclosure also provides recombinant vector including a nucleic acid sequence encoding the polypeptides herein.

Any of the polypeptides of the present disclosure or nucleic acids encoding the polypeptides can be provided in a composition (e.g., a buffer composition or a pharmaceutical composition). The peptide is often formulated with a carrier, buffer, excipient, or diluent. Optionally, the peptide can be in the form of a salt. Further, the polypeptides of the present disclosure can be included in a kit, or detection systems. The kit may include one or more containers filled with one or more of the polypeptides of the present disclosure. Additionally, the kit may include other reagents such as buffers and solutions needed to practice the invention. Optionally associated with such container(s) can be a notice or printed instructions. A kit can include packaging material. As used herein, the phrase "packaging material" refers to one or more physical structures used to house the contents of the kit. The packaging material is constructed by well-known methods, which can provide a sterile, contaminant-free environment.

If desired, the polypeptides of the present disclosure can be modified. The polypeptides of the present disclosure can be chemically bonded with polymers, lipids, other organic moieties, and/or inorganic moieties to increase solubility, stability and etc. For example, the polypeptides can be covalently modified to include one or more water soluble polymer attachments. Useful polymers known in the art include, but are not limited to, polyethylene glycol (PEG) (e.g., PEG approximately 40 kD or 1 kD in size), polyoxyethylene glycol, polypropylene glycol, monomethoxy-polyethylene glycol, dextran, cellulose, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of any of the foregoing. In some embodiments, the polypeptides can be a PEGylated peptide. In addition, chemically synthesized peptides typically carry free amino and carboxy terminal groups, being electrically charged in general. In order to remove this electric charge to prevent interactions with other peptides and/or proteins, peptide ends are often modified, for example, by N-terminal acetylation and/or C-terminal amidation.

Exemplary modifications include, but are not limited to acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Examples of chemically modified amino acids include, but are not limited to:

Acetylated
   N-acetyl-L-alanine, N-acetyl-L-arginine; N-acetyl-L-asparagine; N-acetyl-L-aspartic acid; N-acetyl-L-cysteine; N-acetyl-L-glutamine; N-acetyl-L-glutamic acid; N-acetylglycine; N-acetyl-L-histidine; N-acetyl-L-isoleucine; N-acetyl-L-leucine; N2-acetyl-L-lysine; N6-acetyl-L-lysine; N-acetyl-L-methionine; N-acetyl-L-phenylalanine; N-acetyl-L-proline; N-acetyl-L-serine; N-acetyl-L-threonine; N-acetyl-L-tryptophan; N-acetyl-L-tyrosine; N-acetyl-L-valine Amidated
   L-alanine amide, L-arginine amide Formylated
   N-formyl-L-methionine Hydroxylated
   4-hydroxy-L-proline Lipid Modified
   S-farnesyl-L-cysteine, S-geranylgeranyl-L-cysteine, N-palmitoyl-L-cysteine, S-palmitoyl-L-cysteine, N-myristoyl-glycine, N6-myristoyl-L-lysine Methylated
   N-methyl-L-alanine, N,N,N-trimethyl-L-alanine, omega-N,omega-N-dimethyl-L-arginine L-beta-methylthioaspartic acid, N5-methyl-L-glutamine, L-glutamic acid 5-methyl ester 3'-methyl-L-histidine, N6-methyl-L-lysine, N6,N6-dimethyl-L-lysine, N6,N6,N6-trimethyl-L-lysine, N-methyl-L-methionine, N-methyl-L-phenylalanine Phosphorylated
   omega-N-phospho-L-arginine, L-aspartic 4-phosphoric anhydride, S-phospho-L-cysteine, 1'-phospho-L-histidine, 3'-phospho-L-histidine, O-phospho-L-serine, O-phospho-L-threonine, O4'-phospho-L-tyrosine
Other
L-selenocysteine, L-selenomethionine, L-3-oxoalanine, 2-pyrrolidone-5-carboxylic acid, L-glutamyl 5-glycerylphosphorylethanolamine, 2'43-carboxamido-3-trimethylammonio)propyll-L-histidine (diphthamide), N6-biotinyl-L-lysine, N6-(4-amino-2-hydroxybutyl)-L-lysine (hypusine), N6-retinal-L-lysine.

Modifications can occur anywhere in the polypeptide, including the peptide backbone, the amino acid side-chains and the amino or carboxy termini. The same type of modification may be present in the same or varying degrees at several sites in a given polypeptide. Also, a given polypeptide may contain many types of modifications. Polypeptides may be branched, for example, as a result of ubiquitination, and they may be cyclic, with or without branching.

If desired, the polypeptides of the present disclosure may be labeled, for example, to facilitate detection of the polypeptides. The polypeptides can be labeled by any suitable labels, such as a fluorescent dye, a radioisotope or a contrast agent. Exemplary radioisotopes/fluorescence emitting isotopes can include, but are not limited to, alpha radiation emitting isotopes, gamma radiation emitting isotopes, Auger electron emitting isotopes, X-ray emitting isotopes, fluorescence emitting isotopes, such as $^{18}F$, $^{51}Cr$, $^{67}Ga$, $^{68}Ga$, $^{m}In$, $^{99m}Tc$, $^{140}La$, $^{175}Yb$, $^{153}Sm$, $^{166}Ho$, $^{88}Y$, $^{90}Y$, $^{149}Pm$, $^{177}Lu$, $^{47}Sc$, $^{142}Pr$, $^{159}Gd$, $^{212}Bi$, $^{72}As$, $^{72}Se$, $^{97}Ru$, $^{109}Pd$, $^{105}Rh$, $^{11m15}Rh$, $^{119}Sb$, $^{128}Ba$, $^{123}I$, $^{124}I$, $^{131}I$, $^{197}Hg$, $^{211}At$, $^{169}Eu$, $^{203}Pb$, $^{212}Pb$, $^{64}Cu$, $^{67}Cu$, $^{188}Re$, $^{186}Re$, $^{198}Au$ and $^{199}Ag$. The coupling of the label(s) to the polypeptides may be conducted by any suitable methods, such as by using an activated ester. In particular, in case of coupling label(s) to the amino acids of polypeptides having an amino group in a side chain, activated esters can be used. Alternatively, the following exemplary coupling methods can be used: formation of amides by the reaction of an amine and activated carboxylic acids, disulfide linkage using two thiols or one thiol that specifically reacts with pyridyl disulfides, thioether formation using maleimides or haloacetyls and a thiol component, amidine formation using an imidoester and an amine, hydrazide linkage using carbonyls (e.g. aldehydes) and hydrazides, amine linkage using carbonyls and amines under reductive conditions, and isothiourea formation using isothiocyanates and amines.

The present disclosure also provides fusion proteins or chimeric peptides, which include the polypeptide of the present disclosure. Fusions may be made either at the N-terminus or at the C-terminus of polypeptides disclosed herein. Fusions may be attached directly to the polypeptides with no connector molecule or may be through a connector molecule. A connector molecule may be an atom or a collection of atoms optionally used to link a peptide to another peptide. Alternatively, the connector may be an amino acid sequence designed for cleavage by a protease to allow for the separation of fusion proteins or chimeric peptides. In some embodiments, the fusion proteins or chimeric peptides include a first peptide and a second peptide or protein. In some of these embodiments, the first peptide is often a peptide comprising an amino acid sequence comprising SEQ ID NOs: 1-2. In some of these embodiments, the first peptide can be a peptide having an amino acid sequence as set forth in SEQ ID NOs: 1-2. In some other embodiment, the fusion proteins or chimeric peptides can contain a peptide that is at least about 60%, 70%, 80%, 85%, 90%, 95%, 96%, 97%, 98% or 99% identical to SEQ ID NOs: SEQ ID NOs: 1-2. The second peptide or protein may be different from the first peptide, e.g., the second peptide or protein has an amino acid sequence not substantially identical to the first peptide. The first peptide and the second peptide or protein are operatively linked, e.g., fused, such that the fusion protein or chimeric peptide possesses the activity of both the first peptide and the second peptide or protein. The polypeptides of the present disclosure may be fused to peptides designed to improve certain qualities of the polypeptides, such as binding activity or reduced aggregation. Polypeptides may be fused to an immunologically active domain, e.g., an antibody epitope, to facilitate purification of the polypeptides, or to increase half-life of the polypeptides.

The present disclosure further provides conjugates including the polypeptides disclosed herein. For example, the polypeptides can be conjugated to a detectable substance by coupling (i.e., physically linking). Examples of detectable substances include various enzymes, prosthetic groups, fluorescent materials, luminescent materials and bioluminescent materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin. If desired, the polypeptides can be conjugated to magnetic beads, such as BcMag magnetic beads from Bioclone Inc. (San Diego, Calif.) and streptavidin-immobilized magnetic beads. Polypeptides can also be conjugated to other desired solid supports such as gold nanoparticles, silica or alumina beads and membranes. Additionally, peptide moieties and/or purification tags may be added to the polypeptides. Such regions may be removed prior to final preparation of the polypeptides. In general, the additions of peptide moieties to polypeptides can improve stability, and facilitate purification.

The polypeptides of the present disclosure can bind to EGF. The polypeptide often has a binding affinity for EGF that is less than or equal to $10^{-5}M$, less than or equal to $10^{-6}$ M, or less than or equal to $10^{-7}M$. In some embodiments, binding affinity can be determined using standard assays such as a surface plasmon resonance (SPR) binding assay (for example using Method A described in the Examples). Surface plasmon resonance (SPR) binding analysis methodology is described in, e.g., S. G. Patching, Biochimica et Biophysica Acta 1838 (2014) 43-55 and Drescher et al., Methods Mol Biol. 2009; 493: 323-343. In some embodiments, binding affinity can be determined using Method A described in the Examples. For example, peptide SEQ ID NO: 1 may have a binding affinity of $7 \times 10^{-7}$ M for EGF, using Test Method A. In some embodiments, the polypeptides of the present disclosure can specifically bind to EGF. The term "specifically bind" generally refers to the ability of a polypeptide to bind the epitope or protein of interest with greater affinity than it binds to an unrelated control protein or a negative control (for example, 1% bovine serum albumin (BSA)). For example, the peptide may have a binding affinity for EGF that is at least, 5, 10, 15, 25, 50, 100, 250, 500, 1000, or 10,000 times greater than the binding affinity for a control protein or a negative control. For example, while peptide SEQ ID NOs: 1 has binding affinity to EGF, it does not have a detectable affinity for tumor necrosis factor alpha (TNFα), which indicate specificity for binding to EGF. Generally, the polypeptide has a binding affinity for TNFα), that is greater than $10^{-5}$ M, $10^{-4}$ M, $10^{-3}$ M, or $10^{-2}$ M.

In some embodiments, the peptide or polypeptide of the disclosure binds to EGF with a greater affinity than to TNF-□. In some embodiments, the peptide or polypeptide of the disclosure binds to TNF-□ with less affinity than to EGF. In some embodiments, the binding affinity of a peptide or polypeptide of the disclosure for EGF is at least, 5, 10, 15, 25, 50, 100, 250, 500, 1000, or 10,000 times greater than the binding affinity of the same peptide or polypeptide for TNF-□.

In some embodiments, the peptide or polypeptide of the disclosure has a binding affinity for EGF that is less than or equal to $10^{-6}$ M and a binding affinity for TNF-□ that is greater than or equal to $10^{-5}$ M. In some embodiments, the peptide or polypeptide of the disclosure has a binding affinity for EGF that is less than or equal to $10^{-7}$ M and a binding affinity for TNF-□ that is greater than or equal to $10^{-5}$ M. In some embodiments, the peptide or polypeptide of the disclosure has a binding affinity for EGF that is less than or equal to $10^{-5}$ M and a binding affinity for TNF-□ that is greater than or equal to $10^{-4}$ M. In some embodiments, the peptide or polypeptide of the disclosure has a binding affinity for EGF that is less than or equal to $10^{-5}$ M and a binding affinity for TNF-□ that is greater than or equal to $10^{-3}$ M. In some embodiments, the peptide or polypeptide of the disclosure has a binding affinity for EGF that is less than or equal to $10^{-5}$ M and a binding affinity for TNF-□ that is greater than or equal to $10^{-2}$ M.

The following embodiments are intended to be illustrative of the present disclosure and not limiting.

EMBODIMENTS

Embodiment 1 is a polypeptide comprising a sequence at least 70% identical to SEQ ID NO: 1, wherein the polypeptide comprises no more than 100 total amino acid residues.

Embodiment 2 is the polypeptide of embodiment 1, wherein the polypeptide comprises a sequence at least 80% identical to SEQ ID NO: 1.

Embodiment 3 is the polypeptide of embodiments 1 to 2, wherein the polypeptide comprises a sequence at least 90% identical to SEQ ID NO: 1.

Embodiment 4 is the polypeptide of embodiments 1 to 3, wherein the polypeptide is 100% identical to SEQ ID NO: 1.

Embodiment 5 is the polypeptide of embodiment 1, wherein the polypeptide comprises no more than 50 total amino acid residues.

Embodiment 6 is the polypeptide of embodiment 5, wherein the polypeptide comprises no more than 30 total amino acid residues.

Embodiment 7 is the polypeptide of embodiments 1 to 6, wherein the polypeptide has a binding affinity for EGF that is less than or equal to $10^{-5}$ M.

Embodiment 8 is the polypeptide of embodiments 1 to 7, wherein the polypeptide has a binding affinity for TNFα that is greater than $10^{-5}$ M.

Embodiment 9 is the polypeptide of embodiments 1 to 8, wherein the amino or carboxyl terminus of the polypeptide comprises a cysteine residue.

Embodiment 10 is the polypeptide of embodiments 1 to 9, wherein the polypeptide comprises a sequence at least 80% identical to SEQ ID NO: 2.

Embodiment 11 is the polypeptide of embodiments 1 to 10, wherein the polypeptide comprises a sequence at least 90% identical to SEQ ID NO: 2.

Embodiment 12 is the polypeptide of embodiments 1 to 11, wherein the polypeptide is 100% identical to SEQ ID NO: 2.

Embodiment 13 is the polypeptide of embodiments 1 to 12, wherein the polypeptide binds to EGF with a greater affinity than to TNF-□.

Embodiment 14 is the polypeptide of embodiments 1 to 13, wherein the binding affinity of the polypeptide for EGF is at least 10 times greater than the binding affinity of the polypeptide for TNF-□.

Embodiment 15 is a fusion protein or a conjugate comprising the polypeptide of embodiments 1 to 14.

Embodiment 16 is a composition comprising the polypeptide of embodiments 1 to 14.

Embodiment 17 is DNA encoding the polypeptide of embodiments 1 to 14.

The following working examples are intended to be illustrative of the present disclosure and not limiting.

EXAMPLES

Objects and advantages of this invention are further illustrated by the following examples, but the particular materials and amounts thereof recited in these examples, as well as other conditions and details, should not be construed to unduly limit this invention. These examples are for illustrative purposes only and are not meant to be limiting on the scope of the appended claims.

Materials

Unless otherwise noted, all parts, percentages, ratios, etc., in the examples and in the remainder of the specification are by weight. Commercially available reagents used in the examples and the source from which they were obtained are listed.

Recombinant Human Epidermal Growth Factor (EGF), Recombinant Human Tumor Necrosis Factor-□ (TNF-□), and Anti-EGF-IgG-HRP were obtained from Abcam plc, Cambridge, Mass.

Bovine Serum Albumin (BSA) Lyophilized, and Phosphate Buffered Saline (PBS) (1×) were obtained from the Sigma-Aldrich Corporation, St. Louis, Mo.

Streptavidin-HRP, and Phosphate Buffered Saline with 0.05% Tween 20 (PBST) were obtained from Thermo Fisher Scientific, Waltham, Mass.

HBS-EP Buffer [10 mM 4-(2-hydroxyethyl)-1-piperazineethanesulfonic acid (HEPES), 150 mM NaCl, 3 mM ethylenediaminetetraacetic acid (EDTA), pH 7.4, 0.005% non-ionic surfactant polysorbate 20 (P-20)] was obtained from GE Healthcare Bio-Sciences Corporation, Pittsburgh, Pa.

Peptide Synthesis

Peptides were chemically synthesized by GenScript USA Incorporated (Piscataway, N.J.) using stepwise Solid-Phase Peptide Synthesis (SPPS) methods. Peptides were purified by HPLC to 90% purity and identified by high resolution MALDI-TOF mass spectrometry analysis. N-terminal modification: acetylation and C-terminal modification: amidation were applied. Biotinlyation was also applied for some peptides. Modified peptides were also obtained from GenScript USA. All peptides were stored lyophilized at −20° C. until further use.

Example 1. Dot Blotting Analysis for SEQ ID NO: 1 and SEQ ID NO: 2 with EGF

SEQ ID NO: 1 (1 microliter of a 10 nM solution in PBS containing 3 wt. % DMSO) and SEQ ID NO: 2 (1 microliter of a 10 nM solution in PBS containing 3 wt. % DMSO) were individually spotted at separate sites on a nitrocellulose membrane (obtained from Thermo Fisher Scientific, Waltham, Mass.) and the membrane was dried in air for about 30 minutes. The membrane was then incubated in 25 mL of blocking buffer (3 wt. % BSA in PBS) for one hour at room temperature. The membrane was washed three times (15 minutes for each wash) with 15 mL portions of fresh PBST. The washed membrane was incubated with EGF protein [10 microliters of a 100 ng/mL solution in blocking buffer (3 wt. % BSA in PBS)] with gentle agitation for one hour. The membrane was again washed three times (15 minutes for each wash) with 15 mL portions of fresh PBST. The washed membrane was incubated with anti-EGF-IgG-HRP [1:5000 dilution in 10 mL of the blocking buffer (3 wt. % BSA in PBS)] for one hour with gentle agitation. Following the incubation, the membrane was washed three times (15 minutes for each wash) with 15 mL portions of fresh PBST. The washed membrane was incubated with 10 mL of the development solution for horseradish peroxidase (TMB-Blotting Substrate Solution, Pierce-Fisher Scientific, Rockford, Ill.) with gentle agitation. The color development was stopped by adding water. Dark spots developed on the membrane at the application sites for both SEQ ID NO: 1 and SEQ ID NO: 2 indicating that both SEQ ID NO: 1 and SEQ ID NO: 2 have binding affinity for EGF.

Example 2. Dot Blotting Analysis for Biotinylated SEQ ID NO: 1 with EGF

EGF (1 microliter of a 10 nM solution in PBS was spotted a nitrocellulose membrane (obtained from Thermo Fisher Scientific) and the membrane was dried in air for about 30 minutes. The membrane was then incubated in 15 mL of blocking buffer (3 wt. % BSA in PBS) for one hour at room temperature. The membrane was washed three times (15 minutes for each wash) with 15 mL portions of fresh PBST. The washed membrane was incubated with Biotinylated SEQ ID NO: 1 [10 mL of a 10 ng/mL solution in blocking buffer (3 wt. % BSA in PBS)] with gentle agitation for one hour. The membrane was again washed three times (15 minutes for each wash) with 15 mL portions of fresh PBST. The washed membrane was incubated with Streptavidin-HRP [1:5000 dilution in 10 mL of the blocking buffer (3 wt. % BSA in PBS)] for 30 minutes with gentle agitation. Following the incubation, the membrane was washed three times (15 minutes for each wash) with 15 mL portions of fresh PBST. The washed membrane was incubated with 10 mL of the development solution for horseradish peroxidase (TMB-Blotting Substrate Solution, Pierce-Fisher Scientific) with gentle agitation. The color development was stopped by adding water. A dark spot developed at the application site on the membrane indicating affinity of SEQ ID NO: 1 for EGF.

Example 3. Surface Plasmon Resonance (SPR) Assay with SEQ ID NO: 1 (Test Method A)

The following Test Method A was used for determining the binding affinity (KD) of SEQ ID NO: 1 for EGF and TNF-□□ Binding experiments were performed using Biacore 3000 optical biosensors equipped with research-grade CM5 sensor chips (GE Healthcare Bio-Sciences Corporation). The reagents used for the amine-coupling steps [(1-ethyl-3-(3-dimethylaminopropyl)-carbodiimide (EDC); N-hydroxysuccinimide (NHS); and ethanolamine hydrochloride-NaOH (1 M, pH 8.5)] were obtained from GE Healthcare Bio-Sciences Corporation. In order to efficiently immobilize the peptide on the sensor chips, a modified version of SEQ ID NO:1 was prepared by SPPS in which a "CK" amino acid linker sequence was added to the N-terminal end of the SEQ ID NO: 1 peptide (i.e. linker modified version of SEQ ID NO: 1 for immobilization being CKYVSPGMKNVNWWSHWWHATD). A standard coupling protocol was employed to immobilize the linker modified version of SEQ ID NO: 1 via the lysine residues. The immobilization was performed at 25° C. using HBS-EP as the running buffer. The CM-dextran surfaces of the sensor chip flow cells were activated by a seven minute injection (20 microliters/minute) of freshly prepared 1:1 50 mM NHS: 200 mM EDC. A solution of linker modified SEQ ID NO: 1 in acetic acid (20 mM, pH 5.5) was injected to target 200 response units (RU). The coupling step was followed by a seven minute injection (20 microliters/minute) of ethanolamine hydrochloride-NaOH (1M, pH 8.5) which deactivated residual reactive sites.

The kinetic analysis for EGF was performed at 25° C. The EGF was diluted in HBS-EP buffer and centrifuged at 14,000 rpm for five minutes at 4° C. Individual test samples of EGF at various concentrations (62.5, 125, 250, 500 and 1000 nM) were injected for three minutes at a flow rate of 10 microliters/minute. The surface was regenerated by injection of 10 microliters of glycine-HCl in water (20 mM, pH 2.5).

The kinetic analysis for TNF-□□ was performed at 25° C. The TNF-□□ was diluted in HBS-EP buffer and centrifuged at 14,000 rpm for five minutes at 4° C. Individual test samples of TNF-□□ at various concentrations (62.5, 125, 250, 500 and 1000 nM) were injected for three minutes at a flow rate of 10 microliters/minute. The surface was regenerated by injection of 10 microliters of glycine-HCl in water (20 mM, pH 2.5).

The data analysis was carried out using the BIA Evaluation Software Kit obtained from GE Healthcare Bio-Sciences Corporation. The assay data fitted 1-to-1 Langmuir using global curve fitting analysis. The binding affinity (KD) of immobilized peptide SEQ ID NO: 1 for EGF was measured as $7.06 \times 10^{-7}$ M. No binding of SEQ ID NO: 1 with TNF-□ was observed.

Test Method A can be used to evaluate other peptides and polypeptides of the disclosure for binding affinity to EGF and TNF-□ by replacing the peptide of SEQ ID NO: 1 with other peptides or polypeptides of the disclosure.

Example 4. Surface Plasmon Resonance (SPR) Assay with SEQ ID NO: 2 (Test Method A)

The Test Method A of Example 3 was followed with the exception that a linker modified version of SEQ ID NO: 2 (CKNVNWWSHWWHATD) was immobilized on the sensor chip, instead of SEQ ID NO: 1. The binding affinity (KD) of immobilized peptide SEQ ID NO: 2 for EGF was measured as $2.60 \times 10^{-6}$ M. The binding affinity (KD) of immobilized peptide SEQ ID NO: 2 for TNF-□ was measured as $2.45 \times 10^{-3}$ M.

Example 5. EGF Pull Down Assay with Human Serum

A modified version of SEQ ID NO: 2 was prepared by SPPS in which a "C" amino acid linker was added to the N-terminal end of the SEQ ID NO: 2 peptide (i.e. linker modified version of SEQ ID NO: 2 for immobilization being CKNVNWWSHWWHATD). Peptide SEQ ID NO: 2 was conjugated to BcMag Iodoacetyl functionalized magnetic beads (Bioclone Incorporated, San Diego, Calif.) via the cysteine residue of the linker. The magnetic beads (30 mg) were weighed into a centrifuge tube, suspended in 1 mL of coupling buffer (50 mM Tris, 5 mM EDTA-Na, pH 8.5) and mixed by vortexing for 1-2 minutes. The centrifuge tube was placed in a magnetic separator (Promega Corporation, Madison, Wis.) for 1-3 minutes. The supernatant was then removed and the beads were suspended in 1 mL of coupling buffer by vortexing for 30 seconds. The linker modified version of SEQ ID NO: 2 (0.8 mg) was dissolved in 1.25 mL of coupling buffer containing 20 wt. % dimethyl sulfoxide (DMSO) and 1 mL of this peptide solution was added to the suspension of beads. The beads were incubated for 30-60 minutes at room temperature with gentle rotation. The resulting SEQ ID NO: 2-conjugated beads were sequentially washed (four times) with 1 mL portions of fresh coupling buffer. After washing, the conjugated beads were blocked by adding 1 mL of coupling buffer containing L-cysteine•HCl (8 mg) and then incubating the beads for 30-60 minutes at room temperature with gentle rotation. The conjugated beads were then sequentially washed (four times) with 1 mL portions of fresh aqueous sodium chloride (1 M), suspended in 2 mL of PBS and stored at 4° C.

The wells of a 96 well NUNC MaxiSorp™ microplate (Thermo Fisher Scientific) were blocked with 300 microliters of SUPERBLOCK (PBS) blocking buffer (Thermo Fisher Scientific) for one hour and then sequentially washed (three times) with PBST using a BIO-PLEX ProII wash station (Bio-Rad Laboratories Incorporated, Hercules Calif.). Each test well was then loaded with 20 microliters of the conjugated bead suspension and 200 microliters of human serum (Zen-Bio Incorporated, Research Triangle Park, N.C.). The plate was incubated at 4° C. for one hour. The wells were then blocked using a solution of 3 wt. % BSA in PBS followed by sequential washing (three times) with PBST using the BIO-PLEX ProII wash station. The washed beads were incubated with 50 microliters of acetic acid (20 mM, pH 2.5) for ten minutes and the plate was placed in a magnetic separator for three minutes. The resulting supernatants (40 microliters) were transferred to test wells in a new NUNC MaxiSorp™ microplate. Prior to adding the supernatants, the test wells of the new microplate were filled with 160 microliters of a sodium carbonate-bicarbonate buffer, pH 9.4 (0.2 mM). The microplate as incubated for one hour at room temperature and then sequentially washed (three times) with PBST using a microplate washer (BioTek Instruments Incorporated, Winooski, Vt.). The wells were blocked with 300 microliters of SUPERBLOCK (PBS) blocking buffer (Thermo Fisher Scientific) for one hour and then sequentially washed (three times) with PBST using the microplate washer (BioTek Instruments). Anti-EGF-antibody-HRP (100 microliters at a 1:5000 dilution in PBS) was added to each test well and the plate was incubated for one hour at room temperature. Unbound antibody was removed by sequentially washing (three times) with PBST. The color development solution for horseradish peroxidase activity (100 microliters of 1-STEP Ultra TMB Substrate Solution, available from Thermo Fisher Scientific) was added to each test well. After 50 minutes, 50 microliters of 0.5 M $H_2SO_4$ was added as the stop solution. OD450 absorbance was measured using a SPECTRAMAX M5 plate reader (Molecular Devices, Sunnyvale, Calif.).

As a negative control, the same test procedure as described above was followed using BcMag Iodoacetyl functionalized magnetic beads that were not conjugated to the SEQ ID NO: 2 peptide. The beads for the negative control were prepared according to the following procedure. BcMag Iodoacetyl functionalized magnetic beads (30 mg) were weighed into a centrifuge tube, suspended in 1 mL of coupling buffer (50 mM Tris, 5 mM EDTA-Na, pH 8.5) and mixed by vortexing for 1-2 minutes. The centrifuge tube was placed in a magnetic separator (Promega Corporation) for 1-3 minutes. The supernatant was then removed and the beads were suspended in 1 mL of coupling buffer by vortexing for 30 seconds. The beads were blocked by adding 1 mL of coupling buffer containing L-cysteine•HCl (8 mg) and then incubating the beads for 30-60 minutes at room temperature with gentle rotation. The resulting control beads were sequentially washed (four times) with 1 mL portions of fresh aqueous sodium chloride (1 M), suspended in 2 mL of PBS and stored at 4° C.

The OD450 was measured for the wells containing SEQ ID NO: 2-conjugated beads and for the negative control wells. The mean OD450 (n=3) for the wells with SEQ ID NO: 2-conjugated beads was 0.365±0.04. The mean OD450 (n=3) for the wells with negative control beads was 0.214±0.01. The results show that beads conjugated with SEQ ID NO: 2 pull down more EGF from human serum than unconjugated control beads.

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

| Sequence Listing Free Text | |
|---|---|
| SEQ ID NO: 1 | YVSPGMKNVN WWSHWWHATD |
| SEQ ID NO: 2 | KNVNWWSHWW HATD |

What is claimed is:

1. A polypeptide comprising a sequence at least 70% identical to SEQ ID NO: 1, wherein the polypeptide comprises no more than 100 total amino acid residues.

2. The polypeptide of claim 1, wherein the polypeptide comprises a sequence at least 80% identical to SEQ ID NO: 1.

3. The polypeptide of claim 1, wherein the polypeptide comprises a sequence at least 90% identical to SEQ ID NO: 1.

4. The polypeptide of claim 1, wherein the polypeptide is 100% identical to SEQ ID NO: 1.

5. The polypeptide of claim 1, wherein the polypeptide comprises no more than 50 total amino acid residues.

6. The polypeptide of claim 5, wherein the polypeptide comprises no more than 30 total amino acid residues.

7. The polypeptide of claim 1, wherein the amino or carboxyl terminus of the polypeptide comprises a cysteine residue.

8. The polypeptide of claim 1, wherein the polypeptide comprises a sequence at least 80% identical to SEQ ID NO: 2.

9. The polypeptide of claim 1, wherein the polypeptide comprises a sequence at least 90% identical to SEQ ID NO: 2.

10. The polypeptide of claim 1, wherein the polypeptide is 100% identical to SEQ ID NO: 2.

11. A fusion protein or a conjugate comprising the polypeptide of claim 1.

12. A composition comprising the polypeptide of claim 1.

13. A DNA encoding the polypeptide of claim 1.

* * * * *

SEQUENCE LISTING

<160> NUMBER OF SEQ ID NOS: 2

<210> SEQ ID NO 1
<211> LENGTH: 20
<212> TYPE: PRT
<213> ORGANISM: Artificial Sequence
<220> FEATURE:

```
<223> OTHER INFORMATION: Synthetic peptide

<400> SEQUENCE: 1

Tyr Val Ser Pro Gly Met Lys Asn Val Asn Trp Trp Ser His Trp Trp
1               5                   10                  15

His Ala Thr Asp
            20

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Lys Asn Val Asn Trp Trp Ser His Trp Trp His Ala Thr Asp
1               5                   10
```